United States Patent [19]

Patel et al.

[11] Patent Number: 5,051,250

[45] Date of Patent: Sep. 24, 1991

[54] FIBER CONDITIONING COMPOSITIONS CONTAINING SOLUBILIZED POLY-LOWER ALKYLENE

[75] Inventors: Amrit M. Patel, Dayton; Clarence R. Robbins, Martinsville, both of N.J.

[73] Assignee: Colgate-Palmolive Company, Piscataway, N.J.

[21] Appl. No.: 432,644

[22] Filed: Nov. 7, 1989

Related U.S. Application Data

[63] Continuation-in-part of Ser. No. 369,361, Jun. 21, 1989.

[51] Int. Cl.$^5$ .............................................. A61K 7/075
[52] U.S. Cl. ............................. 424/70; 252/DIG. 13; 424/83
[58] Field of Search ................. 424/70, 83; 252/8.6, 252/DIG. 13

[56] References Cited

U.S. PATENT DOCUMENTS

| | | | |
|---|---|---|---|
| 3,519,562 | 7/1970 | Lanner | 252/8.8 |
| 3,630,949 | 12/1971 | Brux et al. | 252/305 |
| 3,658,985 | 4/1972 | Olson, Jr. et al. | 424/70 |
| 3,749,691 | 7/1973 | Kandathil | 252/8.8 X |
| 3,808,311 | 4/1974 | Olson, Jr. et al. | 424/70 |
| 3,906,091 | 9/1975 | Zviak et al. | 424/70 |
| 3,969,500 | 7/1976 | Kennerley | 424/18 |
| 4,000,077 | 12/1976 | Wixon | 252/8.75 |
| 4,168,302 | 9/1979 | Schoenberg | 424/70 |
| 4,184,970 | 1/1980 | Draper, Jr. | 252/8.8 |
| 4,360,437 | 11/1982 | Wolfes | 252/8.8 |
| 4,387,090 | 6/1983 | Bolich, Jr. | 424/8.8 X |
| 4,401,578 | 8/1983 | Verbruggen | 252/8.8 |
| 4,426,299 | 1/1984 | Verbruggen | 252/8.8 |
| 4,454,049 | 6/1984 | MacGilp et al. | 252/8.8 |
| 4,470,982 | 9/1984 | Winkler | 424/245 |
| 4,472,375 | 9/1984 | Bolich, Jr. et al. | 424/70 |
| 4,610,874 | 9/1986 | Matravers | 424/70 |
| 4,701,322 | 10/1987 | Dixon et al. | 424/70 |
| 4,704,272 | 11/1987 | Oh et al. | 424/70 |
| 4,707,293 | 11/1987 | Ferro | 252/174.17 |
| 4,726,944 | 2/1988 | Osow et al. | 424/70 |
| 4,772,427 | 9/1988 | Dawson et al. | 252/559 |
| 4,818,523 | 4/1989 | Clarke et al. | 424/70 |
| 4,855,130 | 8/1989 | Konrad | 424/70 |

FOREIGN PATENT DOCUMENTS 1601360  10/1981  United Kingdom .

OTHER PUBLICATIONS

"A Formulary of Cosmetic Preparations", Michael & Irene Ash, Chemical Publishing Co., N.Y., N.Y., 1977, Chapter II, pp. 26, 64.
Cosmetics, Science and Technology, 2nd ed., vol. 3, John Wiley & Sons, 1974, p. 142.

Primary Examiner—Thurman K. Page
Assistant Examiner—Susan S. Rucker
Attorney, Agent, or Firm—Richard J. Ancel; Robert C. Sullivan; Murray M. Grill

[57] ABSTRACT

A fiber conditioning composition, especially useful for conditioning human hair on the head, includes a cationic surface active fiber conditioning agent, such as a hair conditioning quanternary ammonium halide, a normally solid and water insoluble poly-lower alkylene, such as polyethylene, and a hydrocarbon solubilizer for such poly-lower alkylene, such as mineral oil, which liquefies it and makes it water dispersible in the presence of the cationic surface active fiber conditioning agent and water, which composition is of a significantly increased fiber conditioning effect compared to control compositions containing the cationic surface active fiber conditioning agent alone. In a preferred form the fiber conditioning composition includes water and anionic synthetic organic detergent, and is a shampoo for human hair.

The invention also is of processes for conditioning fibrous materials, including shampooing of human hair and conditioning it so that wet combing, dry combing and manageability are improved and static charge thereon and objectionable "flyaway" are reduced. The invention also includes processes for manufacturing the invented fabric conditioning compositions and shampoos.

14 Claims, No Drawings

FIBER CONDITIONING COMPOSITIONS CONTAINING SOLUBILIZED POLY-LOWER ALKYLENE

This application is a continuation-in-part of U.S. patent application Ser. No. 07/369,361, which was filed on June 21, 1989.

This invention relates to fiber conditioning compositions. More particularly, it relates to such compositions which are shampoos that include liquefied poly-lower alkylene and which leave shampooed hair better conditioned (easier to comb, more manageable and lower in static charge) after shampooing.

Fiber conditioning compositions, such as compositions for treating washed fibrous materials, which have included fabric softeners, which condition washed fabrics by making them softer and less likely to hold static charges after drying in an automatic laundry dryer, have contained cationic conditioning agents, such as quaternary ammonium halides, and such quaternary ammonium compounds have also been included in hair rinses. Also, polyethylene has been employed in preparations for treating fibrous materials, including human hair, sometimes as a lubricant for such materials. Mineral oil has also been applied as a lubricant and as a lustering agent to fibers, including hair. Similarly, such materials have been incorporated in shampoos, some of which were based on anionic synthetic organic detergents. However, it is believed that the present invention is novel and that it was not previously known that a normally liquid hydrocarbon, such as mineral oil, could be employed in the presence of cationic surface active fiber conditioning agent to solubilize or liquefy a normally water insoluble poly-lower alkylene, prior to dispersing it in water, and that such dispersed poly-lower alkylene, such as polyethylene, in the presence of cationic surface active fabric conditioning agent, would significantly improve the conditioning of fibrous materials, especially human hair, after it was treated with such a conditioning composition, in the form of an anionic synthetic organic detergent shampoo.

In accordance with the present invention a fiber conditioning composition comprises a cationic surface active fiber conditioning agent, a normally water insoluble poly-lower alkylene and a solubilizer for such poly-lower alkylene, which makes it water dispersible in the presence of the cationic surface active fiber conditioning agent and water, so that the dispersed poly-lower alkylene significantly increases the fiber conditioning effect of the cationic surface active fiber conditioning agent. The invention also relates to such compositions which are in the form of an anionic synthetic organic detergent shampoo, and to uses of such compositions (and shampoos) and to the manufacturing thereof.

The cationic surface active fiber conditioning agent, which is the primary conditioning agent in the fiber conditioning composition, is preferably a quaternary ammonium salt, although other cationic surface active compounds with fiber conditioning properties may also be employed, at least in part. Thus, imidazolinium salts and betaines and such cationic materials as are described in U.S. Pat. No. 4,000,077 may be substituted, as may be complexes of cationic surfactants with anionic surfactants and with organic acids, such as citric acid. Such complexes are described in U.S. Pat. Nos. 4,888,119, 4,786,422, and 4,929,367.

The preferred quaternary ammonium salts are of the formula $R^1 R^2 R^3 R^4 N^+ X^-$ wherein at least one R is lower alkyl and at least one is higher alkyl, with the others being higher and/or lower alkyl. Preferably $R^1$ is lower alkyl, such as of 1 to 4 carbon atoms, $R^2$ and $R^3$ are higher alkyls of 10 to 40 carbon atoms, $R^4$ is such a lower alkyl or such a higher alkyl, and X is a salt-forming anion, such as halide, lower alkanol sulfate, or lower carboxylic acid radical, e.g., chloride, bromide, methosulfate, ethosulfate or acetate. The lower alkyl will normally be of 1 to 3 or 4 carbon atoms, preferably being of 1 or 2 carbon atoms, more preferably being methyl, and the higher alkyl will be of 10 to 40 carbon atoms, preferably 12 to 18, 20 or 22 carbon atoms, more preferably 14 or 16 to 18 or 22 carbon atoms, e.g., 16 or about 16. The anion is preferably a halogen, such as chlorine, bromine or iodine, with chlorine and bromine being preferred and with chlorine being more preferred.

The number of lower alkyls will preferably be 1 or 2 and the number of higher alkyls will normally be 2 or 3. It has been found desirable to have the total number of carbon atoms in the quaternary ammonium salt at least 30 and preferably at least 34, and most preferably the quaternary ammonium salt will include three higher alkyls and one lower alkyl and will be a chloride. The most preferred higher alkyl is cetyl, the most preferred lower alkyl is methyl, and the most preferred quaternary ammonium halide is tricetylmethyl ammonium chloride. Nevertheless, it is within the invention to employ other quaternary ammonium halides, such as distearyl dimethyl ammonium chloride, dilauryl dimethyl ammonium bromide, stearyl cetyl dimethyl ammonium chloride, and other hair conditioning cationic surfactants as at least part of the fiber conditioning cationic surfactant (or surface active agent) content of the present compositions.

A secondary fiber conditioning component of the present composition is normally solid water insoluble poly-lower alkylene. Such polymer is of a solubility less than 1 g./100 ml. water and often is of a solubility less than 0.1 g./100 ml. water. In aqueous media even when it is present in very finely divided form, it imparts little conditioning to fibrous materials, such as human hair, to which such aqueous compositions are applied, and it has a similar low conditioning activity from other media that are suitable for application to fibrous materials to be conditioned. However, in the present compositions, when employed in conjunction with normally liquid hydrocarbon, such as mineral oil, the water insoluble poly-lower alkylene is activated and in conjunction with the cationic surface active fiber conditioning agent, also present in the invented compositions, surprisingly increases fiber conditioning effects of such cationic conditioning agent.

Although various poly-lower alkylenes may be employed as the secondary conditioning agent, such as polymers of hydrocarbons of 1 to 5 carbon atoms each, with molecular weights of the polymers in the range of 1,000 to 10,000 or more, with some useful improvement in conditioning of the cationic conditioning agent being realizable, such polymers are normally those of ethylene or propylene and may be considered to be straight chains of methylene groups or with varying amounts of branching and will normally be of molecular weights in the range of 1,000 to 5,000, preferably 1,000 to 4,000, more preferably 2,000 to 2,500, and most preferably 2,000 or 2,100 or about 2,000. Oxidized versions of these poly-alkylene polymers may also be used which can create larger hydrocarbons with terminal carboxyl groups. Such polymers, especially those which are most preferred, will be dispersible in aqueous media which also contain anionic synthetic organic surface active agents or detergents, when in the presence of a liquefying proportion of mineral oil or other relatively low molecular weight hydrocarbon (normally in liquid state) or equivalent solubilizer for the poly-lower alkylene.

The solubilizer for the poly-lower alkylene is one which makes it water dispersible in the presence of the cationic surface active fiber conditioning agent and water and also in the presence of anionic synthetic organic surfactant or detergent. The result of employing the solubilizer is that the normally solid water insoluble poly-lower alkylene is solubilized so that it can be dispersed and will remain suspended in an aqueous medium without objectionable phase separation or settling out of the polymer. Also, and surprisingly, the presence of the solubilizer significantly improves the fiber conditioning effect of the cationic surfactant, possibly because of the increased effect of the secondary conditioning agent. The solubilizer is preferably a normally liquid hydrocarbon which will usually be of a molecular weight in the range of 150 to 1,000, preferably 300 to 800, more preferably 400 to 700, and most preferably 500 to 600, e.g., 550 or about 550.

The hair conditioning composition may be in any suitable form and may be utilized in varying conditioning applications. It is preferably in liquid form, often in an aqueous medium, but it may be employed in other useful forms too. Thus, it may be in gel, paste, creme, foam or aerosol form or can even be in solid form (bar) and thus may be dispersed in water or other aqueous medium in use. Preferred compositions of the invention are shampoos which will usually, include a synthetic organic detergent, such as an anionic detergent, and water. Optionally, amphoteric, ampholytic, zwitterionic and nonionic detergents and surfactants may be utilized in such shampoos instead of or with the anionic detergent(s). Various suitable such detergents are listed in *McCutcheon's Detergents and Emulsifiers,* North American Edition, 1984. The preferred anionic detergents, which are also described therein, may be designated as "sulf(on)ated". Such are water soluble lipophile sulfates and/or sulfonates of 8 to 22 carbon atoms, preferably of 10 to 18 carbon atoms, more preferably of 10 to 16 or 18 carbon atoms and most preferably of 12 to 16 or 18 carbon atoms. Among such anionic detergents there may be mentioned, as exemplary thereof, higher alkyl sulfates, paraffin sulfonates, olefin sulfonates, monoglyceride sulfates, higher fatty alcohol lower alkoxy sulfates, and linear higher alkylbenzene sulfonates. The most preferred of the higher alkyl sulfates are those of 12 to 16 carbon atoms and the most preferred of the higher alkyl lower alkoxy sulfates are of 16 to 18 carbon atoms, with the higher alkyl thereof being lauryl and with 2 or 3 ethoxy groups per mole. However, such alkyls may desirably be of 12 to 16 carbon atoms and the alkoxy content may be from 1 to 20, such as 2 to 6 ethoxies per mole. A most preferred higher fatty alcohol sulfate is lauryl sulfate and a particularly preferred higher fatty alcohol poly-lower alkoxy sulfate is the sulfated di- or tri-ethoxylated lauryl alcohol. Most preferably the anionic detergent will be a mixture of higher alkyl sulfate and higher alkyl ether sulfate, with either being present in greater proportion, with the ratio of amounts of such components usually being in the range of 10:1 to 1:10 or 7:1 to 1:7, e.g., 1:5 and 5:1. The anionic detergents will be employed in the forms of their water soluble salts, which will usually be salts of alkali metals (e.g., sodium, potassium), ammonium, amines, (such as dimethyl amine and trimethyl amine) or lower alkanolamines (such as triethanolamine, diethanolamine and monoethanolamine). Exemplary of useful detergents are ammonium lauryl sulfate, sodium lauryl diethoxy sulfate, ammonium lauryl triethoxy sulfate, sodium alpha $C_{16}$ olefin sulfonate, sodium $C_{14}$ paraffin sulfonate, sodium coco monoglyceride sulfate, triethanolamine cetyl sulfate and dimethyl amine myristyl sulfate. However, for best results, it is preferred to utilize higher alkyl sulfate or a mixture of higher alkyl sulfate and higher alkyl ether sulfate, such as lauryl sulfate and lauryl diethoxy or triethoxy sulfate, with the higher alkyl sulfate being present in greater proportion, and with the ammonium or triethanoamine anionic detergent salt also being present in greater proportion.

The water employed in the aqueous compositions of the invention, including the preferred shampoos, will preferably be deionized water of a hardness content less than 10 parts per million, as calcium carbonate, but other waters may also be utilized when circumstances require. So as to ensure that the invented compositions are free of microorganisms it is preferred to use irradiated deionized water, and the various mixing vessels, tanks, piping and containers employed will be maintained scrupulously clean.

In addition to the required components of the invented conditioning compositions and the shampoos, which are preferred embodiments thereof, there may also be present in them various adjuvants which are known in the art to impart desirable properties to such compositions, or which have been determined by the present inventors or their fellow researchers to have desirable effects when incorporated in the invented compositions. Among such adjuvants may be mentioned paraffins, petrolatums, microcrystalline waxes and isoparaffins (all of which may act as solubilizing hydrocarbons, in supplementation of the mineral oil), higher fatty acid esters of lower alcohols, lower fatty acid esters of higher alcohols, and higher fatty acid esters of higher alcohols, such as are described in U.S. patent application Ser. No. 07/369,361 as being useful for improving hair conditioning effects of fiber treating compositions, such as shampoos; thickeners, such as lower alkyl celluloses and hydroxy-lower alkyl celluloses, and gums, such as xanthan gum, which may also act as stabilizers; foam modifiers and improvers, such as betaines, higher fatty acid triglycerides, and lower alkanolamides, e.g., cocoamidopropyl betaine, $C_{18-36}$ acids triglyceride and lauric monoethanolamide; pearlescing agents, such as ethylene glycol mono- and distearates; supplemental conditioning agents, such as silicones and amino-substituted silicones (such as are described in our patent application entitled Fiber Conditioning Compositions Containing Aminosilicone Contioning Agent, that was filed on the same date as the present application); anti-dandruff agents, such as zinc pyrithione; viscosity control agents, such as propylene glycol and sodium chloride; preservatives and antioxidants; anti-freezes, such as ethylene glycol; sequestrants, such as EDTA; pH adjusters, such as citrates and citric acid; colorants (dyes and dispersible pigments); and solvents, such as ethanol and isopropanol.

The proportions of the various components of the invented compositions are such as to produce the desired significant increase in fiber conditioning effects. Such improvements in fiber conditioning effects of the conditioning composition are obtained when the proportion of cationic surface active fiber conditioning agent is a fabric conditioning proportion, the proportion of normally solid, water insoluble polyethylene is such proportion as is sufficient to increase the fabric conditioning effect of the cationic agent when the polyethylene is dispersed in water, and the proportion of liquid state hydrocarbon or mixture of hydrocarbons is such as to help to liquefy the normally solid polyethylene and make it water dispersible in the presence of the mentioned amount of quaternary ammonium salt and water. For hair conditioning compositions which contain anionic synthetic organic detergent, and for shampoos which contain such anionic detergent and water, the proportion of anionic detergent will be a surface active proportion thereof and often will be a detersive proportion, depending on the application intended, and the proportion of water will be sufficient to form a continuous medium when such is to be produced, as in the case of shampoos.

For shampoos the proportions of components will normally be in ranges of 8 or 10 to 25, 30 or 35% of lipophile sulfate and/or sulfonate, preferably 8 to 20%, more preferably 10 to 15% of alcohol sulfate or alcohol ether sulfate and 1 to 5% of alcohol ether sulfate or alcohol sulfate, more preferably 10 or 11 to 13 or 14% of alkyl sulfate and 1 to 4% of alkyl ether sulfate, e.g., 12.5% of ammonium lauryl sulfate and 2.5% of sodium lauryl diethoxy ether sulfate. The corresponding percentages for the cationic hair conditioning agent or quaternary ammonium salt are normally of 0.1 to 3%, preferably 0.2 to 2%, more preferably 0.3 to 1 or 1.5%, still more preferably 0.3 to 0.7%, and most preferably 0.4 to 0.6%, e.g., about 0.5%. The content of normally solid polyethylene will usually be in the range of 0.1 or 0.2 to 5%, preferably 0.2 to 1.5 or 2%, more preferably 0.2 or 0.5 to 1% and usually most preferably 0.3 or 0.5 to 0.9%, e.g., about 0.4% and 0.75%. The ranges of concentrations for the mineral oil are normally 0.1 to 10%, preferably 0.2 to 8%, more preferably 0.5 to 6% and most preferably 0.7 to 5%, e.g., about 1% or about 4%. The ranges of total adjuvant content are normally 0.1 to 30%, preferably 0.5 to 20% and more preferably 3 to 15%. Ranges for water contents are normally 50 to 95%, preferably 60 or 70 to 90% and most preferably 65 to 80%, e.g., about 73%. For non-aqueous compositions the required components, cationic conditioner, poly-lower alkylene and mineral oil, are in the same relative proportions and the aqueous medium may be omitted or may be replaced, in whole or in part, by other solvent or liquid medium, e.g., ethanol or isopropanol.

The ranges of proportions for the various adjuvants or other unrequired components of the invented compositions, which may be present together or in any of various combinations, include: 0.1 to 2%, preferably 0.1 to 1%, and more preferably 0.1 to 0.5%, e.g., about 0.25% or 0.3% of isoparaffin of 10 to 18 carbon atoms, preferably of 12 to 16 carbon atoms and more preferably of 13 to 14 carbon atoms; 0.1 to 2%, preferably 0.1 to 1%, and more preferably 0.1 to 0.5%, e.g., about 0.35% or 0.4% of paraffin of 20 to 60 carbon atoms, preferably 20 to 50 carbon atoms, and more preferably 20 to 40 carbon atoms; 0.05 to 1.5%, preferably 0.2 to 1%, and more preferably 0.4 to 0.8%, e.g., about 0.6%, of cellulosic thickening agent, which is preferably a hydroxy-lower alkyl cellulose thickening agent, more preferably hydroxyethyl cellulose or a mixture of hydroxyethyl celluloses; 0.5 to 6%, preferably 2 to 5%, more preferably 2 to 4%, e.g., about 3.5%, of higher fatty acid lower alkanolamide (wherein the higher fatty acid is of 12 to 18 carbon atoms and the lower alkanol is of 2 to 3 carbon atoms), which is preferably a higher fatty acid monoethanolamide and more preferably is lauric monoethanolamide or lauric-myristic monoethanolamide; 0.5 to 1.5%, preferably 0.5 to 1%, more preferably 0.7 to 0.9%, e.g., about 0.8%, of lower alkylene glycol higher fatty acid ester, preferably ethylene glycol higher fatty acid diester, such as ethylene glycol distearate; 0.1 to 1%, preferably 0.1 to 0.6%, more preferably 0.2 to 0.5%, e.g., about 0.4%, of higher fatty acid ester of higher fatty alcohol, preferably $C_{12-18}$ higher fatty acid ester of $C_{12-18}$ fatty alcohol, more preferably $C_{16-18}$ fatty acid ester of $C_{16-18}$ fatty alcohol, e.g., stearyl stearate; 0.3 to 2%, preferably 0.5 to 1.5%, more preferably 0.5 to 1%, e.g., about 0.8%, of $C_{18-36}$ acid triglyceride; 0.2 to 1%, preferably 0.3 to 0.7%, more preferably 0.4 to 0.6%, e.g., about 0.5 or 1%, of preservative or antioxidant; up to 0.5 or 1%, preferably up to 0.3% of alkali metal chloride, preferably sodium chloride; and up to 0.1% of ether citric acid or alkali metal citrate for pH adjustment (which adjustment should be to a pH in the range of 5.0 to 8.0, preferably 6.0 to 7.0, e.g., about 6.5).

As was previously mentioned, the fiber conditioning and hair conditioning compositions of the invention may be in various physical forms, but a preferred form is liquid and a preferred embodiment of the invention is a hair conditioning shampoo. Such compositions, to be acceptable in the market place, should be stable chemically and physically, not deteriorating to an unacceptable extent on storage (especially not losing improved conditioning properties), and not separating or settling or changing objectionably in viscosity. The invented shampoos are of desirable viscosities in the range of 1,000 to 15,000 centipoises at room temperature (25° C.), preferably being in the range of 3,000 to 6,000 cp. and more preferably being of a viscosity of about 3,500 or 4,000 centipoises at such temperature. The invented shampoos do not settle on storage and substantially maintain their improved hair conditioning properties. Also, viscosities remain about the same as when the shampoos were made, with some expected increase therein soon after completion of manufacturing, so that approximately the desired use viscosity may be designed into the product.

The improved hair conditioning compared to controls, from which both the polyethylene and mineral oil have been omitted, is noticeable to the casual user of the conditioning composition or shampoo and is measurable in standard tests used to evaulate ease of wet combing, ease of dry combing, and manageability and static charge retention (related to objectionable flyaway). The casual shampooer will note that after shampooing with the invented composition the hair is easier to comb, both wet and dry, than a control, is more manageable and is less subject to static charge accumulations and objectionable flyaway. Scientific tests also prove that the force required to move a comb through a standard hair tress after treatment of the hair with an invented conditioning composition or after shampooing with an invented shampoo (and rinsing) is less than when a control is employed for similar purposes. Also, flyaway hair is less apparent than when a control product is used to shampoo the tresses. Such results are confirmed by panel tests, in which several experienced evaluators, utilizing both the experimental and control product in blind tests, evaluate them for such combing, static and manageability characteristics.

Uses of the invented compositions, including shampoos, are not required to be different from normal uses of hair conditioning compositions and shampoos. Conditioning agents may be applied at room temperature or at somewhat elevated temperatures in normal quantities and may be left on the hair for different lengths of time, depending on the extent of conditioning desired. Usually, the conditioning agent and the hair will be at a temperature in the range of 15° C. to 50° C., preferably 20° C. to 40° C., and the conditioning composition will be in contact with the hair for from 30 seconds to ten minutes, preferably one to five minutes. The amount of composition applied will normally be in the range of 0.1 to 25 grams, often 0.2 to 10 g. and frequently 0.5 to 2 g., on the basis of the non-aqueous and non-solvent (nonalcoholic) components of the compositions. On the basis of the shampoo which may be employed, such application rates may be in the range of 0.5 to 50 grams, often 2 to 15 or 20 grams and frequently five to ten grams per use. The applied composition may be brushed and/or combed through the hair and may be subsequently washed out, may be allowed to remain on the hair or may be partially removed, as by towelling. When the shampoo is employed to wash and condition the hair it will be rinsed off with water after remaining on the hair as an aqueous foam for a sufficient length of time, usually 1 to 5 minutes, to satisfactorily condition the hair, and may then be wet combed, dried, as by blow drying, and dry combed or brushed to the desired style.

To manufacture the present compositions, including shampoos, no special measures need be followed, but to obtain best stability of the shampoos and aqueous products on storage and while being used it will be most desirable to form a dispersion of the water soluble lipophile sulfate and/or sulfonate and adjuvants in water at an elevated temperature, such as 60° or 70° to 90° C., dissolve and/or disperse cationic conditioning agent, such as quaternary ammonium halide, with the normally solid polyethylene in a liquid mineral oil at elevated temperature (70° to 90° C.) and admix the two solutions and/or dispersions to form a stable dispersion. When adjuvants are present those which are water soluble and/or dispersible may be mixed in with the aqueous phase materials and those which are not soluble or dispersible in the aqueous medium, such as paraffin, isoparaffin and microcrystalline wax, may be blended in with the three mentioned lipophilic materials, or in some instances may be added to the mixture of the aqueous materials and lipophilic materials either before or after cooling thereof to room temperature. Normally, perfumes are added to the other mixed components after such cooling so as to avoid losses thereof due to volatilizations of components or degradation when heated. When the procedure described is not followed, as when components are blended indiscriminately, unstable products may result, which separate or settle out on storage, and such unstable compositions tend to have poorer conditioning properties than the stable conditioning compositions and shampoos that are made according to the invented procedure.

The following examples illustrate but do not limit the invention. Unless otherwise indicated all parts are by weight and all temperatures are in °C.

EXAMPLE 1

| Component | Percent (by weight) A (invention) | Percent (by weight) B (control) |
| --- | --- | --- |
| * Natrosol TM 250HR | 0.45 | 0.45 |
| ** Natrosol 330PA | 0.15 | 0.15 |
| Ammonium lauryl sulfate | 12.50 | 12.50 |
| *** Sodium lauryl ether sulfate | 2.50 | 2.50 |
| Lauric monoethanolamide | 3.50 | 3.50 |
| Ethylene glycol distearate | 0.75 | 0.75 |
| Stearyl stearate | 0.35 | 0.35 |
| Propylene glycol, U.S.P. | 0.50 | 0.50 |
| **** Syncrowax TM HGC-L | 0.75 | 0.75 |
| + Britol TM /50 | 4.00 | — |
| ++ AC Polyethylene 9A (drop point of 117° C., M.W. in range of 2,000–4,000) | 0.4 | — |
| +++ Tricetyl methyl ammonium chloride | 0.50 | 0.50 |
| ++++ Germaben TM II | 0.50 | 0.50 |
| Colorant (dye and/or water dispersible pigment) | 0.10 | 0.10 |
| Sodium chloride | 0.10 | 0.10 |
| Citric acid | 0.01 | 0.01 |
| Water, deionized and irradiated | 72.44 | 76.84 |
| Perfume | 0.50 | 0.50 |
| | 100.00 | 100.00 |

* Hydroxyethyl cellulose (Hercules Corp.)
** Hydroxyethyl cellulose (Hercules Corp.)
*** Ether group = diethoxy
**** $C_{18-36}$ acid triglyceride (Croda Corp.)
+ Mineral oil, of m.w. in the range of 400 to 800 (Witco/Penreco Corp.)
++ Polyethylene homopolymers, of M.W. in the range of 2,000 to 4,000, drop point of 117° C. (Allied Signal, Inc.)
+++ Trade name is PC-90 (Sherex Chemical Corp.)
++++ Preservative (Sutton Laboratories, Inc.)

The conditioning composition of the A formula given above is made by heating together the water soluble and water dispersible materials of the formula, with all or substantially all of the water of the formula (if less than all the water is used at this stage the rest is added to the mix of heated aqueous portion and of the heated lipophilic melt or dispersion), heating together the polyethylene, mineral oil, paraffin wax and any other "liquid" hydrocarbons to a temperature of about 80° C. and mixing together the heated pre-mixes, with stirring, for ten minutes, which produces a stable shampoo that does not separate or settle out after storage for a month at elevated temperature, which is equivalent to storage for at least a year at room temperature. The shampoo made is tested for conditioning properties by a panel of at least five experienced evaluators of such products, for conditioning effects, and the panel members test hair tresses and/or hair on the head that is shampooed with such composition, rinsed with water and dried, evaluating the hair with respect to various conditioning characteristics, including ease of wet combing, ease of dry combing, static charge, flyaway and manageability.

In a similar manner a control shampoo (B) is made, which is of the same formula as the A shampoo except for the omission of the polyethylene and the mineral oil, which are replaced by water. Both compositions are of pH's of approximately 6.5 and of viscosities, at 25° C., of about 3,500 or 4,000 centipoises. Hair tresses shampooed with such control composition, followed by rinsing and drying, in the same manner as practiced with respect to the A composition, are evaluated by the panel members and the evaluations are compared to those for the hair shampooed by the A composition, as described, followed by rinsing and drying it. The panel members find that overall conditioning effects from using the A composition are significantly better than those for the B composition. With evaluations numerically on a scale of 1 to 5, with the higher the number the better the conditioning, the ratings are about 2 for the B treatment and about 5 for the A treatment.

EXAMPLE 2

| Component | Percent (by weight) |
|---|---|
| Ammonium lauryl sulfate | 12.50 |
| * Sodium lauryl ether sulfate | 2.50 |
| Coco diethanolamide | 3.50 |
| Natrosol 250HR | 0.45 |
| Natrosol 330PA | 0.15 |
| Ethylene glycol distearate | 0.75 |
| Stearyl stearate | 0.35 |
| Propylene glycol, U.S.P. | 0.50 |
| Syncrowax HGC-L | 0.75 |
| ** Paraffin wax (m.p. = 36° C.) | 0.35 |
| Britol/50 | 1.00 |
| *** AC Polyethylene 617A | 0.75 |
| **** Isopar TM M | 0.25 |
| Tricetyl methyl ammonium chloride | 0.50 |
| Germaben II | 0.50 |
| Sodium chloride, crystalline | 0.10 |
| Citric acid (or sodium citrate, when pH is too acidic) | 0.01 |
| Water, deionized and irradiated | 74.34 |
| Perfume | 0.75 |
| | 100.00 |

* Sodium lauryl diethoxy or triethoxy ether sulfate
** $C_{20-40}$ straight chain paraffins
*** Polyethylene homopolymer, of M.W. in the range of 2,000 to 4,000
**** $C_{13-14}$ isoparaffins A shampoo of the above formula is made in the same manner as described for manufacture of the shampoo of Example 1, and the melt of lipophilic materials includes polyethylene, mineral oil, paraffin wax and isoparaffin. The resulting shampoo is of a pH of about 6.5 and a viscosity of about 3,500 or 4,000 centipoises at 25° C., and is stable on storage, maintaining its initial improved hair conditioning properties and not settling out, separating or otherwise deteriorating on storage for up to a year.

When tested against a control shampoo of the same formula except for the omission of the polyethylene it is measurably better in hair conditioning properties, which evaluation is based on a totality of wet combing ease, dry combing ease, greater manageability, less static and less flyaway for hair tresses shampooed with the invented formula, compared to tresses shampooed with the control.

In the above formula the anionic detergents are changed, proportions thereof are modified, supplemental hair conditioning agents are added, and it is confirmed that the presence of the polyethylene, as solubilized by the mineral oil, desirably improves the conditioning characteristics of the hair conditioning shampoo. The invented products of Examples 1 and 2 are considered to be significant improvements over prior art conditioning shampoos of such types primarily because of the presence therein of the poly-lower alkylene conditioning agent in conjunction with the mineral oil and the cationic conditioning surfactant. The differences in conditioning are not merely noticeable by instrumental testing or by trained observers but are apparent to the average consumer, the user of such products. The shampooed hair is noticeably easier to comb out in wet condition and to brush and comb in dry condition. It is easier to set and is more manageable, at least in part because of a lower static charge being generated thereon and because there is less tendency for the hairs to repel each other, which repellent actions cause objectionable flyaway.

The compositions described in Examples 1 and 2 are hair conditioning shampoos but the invention is also applicable to the formulating of fiber conditioners and to nonshampoo hair conditioning compositions. Thus, such products may be applied to other natural fibers, such as cotton, linen and wool, and to synthetics, such as nylons, polyesters, acrylics, and acetates, to condition them. Also, when the required cationic conditioners, polyethylene and mineral oils of the Examples 1 and 2 compositions are employed in solutions in alcoholic or other suitable solvents or are converted to gel or other suitable form and are applied to the hair, as by spraying thereon, applying as a liquid and brushing in, or applying as a gel and rubbing into the hair, the hair is noticeably conditioned by such applications. When such applications are made from aqueous systems better conditionings are obtained than when the mineral oil and any other solubilizing hydrocarbons are omitted from the compositions (in which case the shampoos cannot be made in usable condition because the polyethylene will not be satisfactorily dispersed or emulsified).

EXAMPLE 3

When, in variations of the formulations of Examples 1 and 2, the various adjuvants are omitted from the formulas so that the shampoos made contain only the required constituents thereof, the anionic surfactant, cationic surfactant conditioner, polyethylene, solubilizing liquid hydrocarbon (mineral oil) and water, the shampoos made are less viscous than is desirable but are usefully employable to shampoo and condition hair. When the mineral oil is omitted from the formulas the polyethylene cannot be dispersed or emulsified in the system. When, instead of the described mineral oil, other lighter and heavier mineral oils and other normally liquid hydrocarbons are employed to solubilize the polyethylene, improvements in conditioning over uses of similar compositions that do not contain such solubilizing agents are obtainable but sometimes such other hydrocarbons can be cosmetically unacceptable or toxic. Mineral oil is considered to be innocuous, it helps to impart a luster to the shampooed hair and often it functions as a better solubilizer for the polyethylene, all of which makes it a more highly preferred solubilizing agent in the invented compositions.

When the compositions of the invention are modified by changing any of the various required components of the invented conditioning compositions and shampoos of the Examples to others of the components mentioned in the specification, such as by replacing the anionic detergent(s) with triethanolamine lauryl sulfate, sodium myristyl sulfate, potassium cetyl sulfate, triethanolamine myristyl diethoxy sulfate, sodium $C_{14}$ paraffin sulfonate, ammonium $C_{10}$ olefin sulfonate, or triethanolamine coco monoglyceride sulfate or mixtures thereof, replacing the polyethylene with higher or lower molecular weight polyethylenes within the 1,000 to 10,000 molecular weight range mentioned, such as Allied Signal's AC Polyethylenes 6A, 7A, 8A and 725, and Eastman Chemical Corporation's E-12, -14 and -43 (M.W's. of 1,800, 2,300 and 4,500), replacing the mineral oil with mineral oils of molecular weights of about 550 or of higher or lower molecular weights, up to 1,000 or down to 150, or replacing the cationic surfactant, at least in part, with distearyl dimethyl ammonium chloride, trilauryl methyl ammonium chloride, stearyl cetyl dimethyl ammonium chloride or dilauryl diethyl ammonium chloride, desired hair conditioning and cleaning effects are also obtainable, and are greater when the combination of polyethylene and mineral oil is present than when it is omitted. Also, in such compositions the various illustrated adjuvants or some of them may be present or may be omitted. Preferably, in addition to or in replacement of other optional conditioning agents mentioned there will be present an aminosilicone, such as been described in U.S. Pat. Nos. 4,559,227, 4,563,347, 4,601,902, 4,704,272, and 4,749,732, and in the application Ser. No. 07/432,952 of the present inventors which is being filed the same day as the present application and which is entitled "Fiber Conditioning Compositions Containing Aminosilicone Conditioning Agent" an which is incorporated herein by reference. Preferably, the amount of such aminosilicone hair conditioning agent will be 0.05 to 3%, preferably 1 to 2%, on the shampoo formula basis. In the various conditioning composition formulas the proportions of components may also be changed, being increased or decreased by 10%, 20% and 30%, so long as they are retained within the ranges recited in the specification, and the mentioned improved conditioning effects are obtainable.

The various patents, texts, publications, specifications and applications previously referred to in this specification are hereby incorporated herein by reference.

The invention has been described with reference to illustrations and examples thereof but is not to be limited to these because it is evident that one of skill in the art, with the present specification before him or her, will be able to utilize substitutes and equivalents without departing from the invention.

What is claimed is:

1. A hair conditioning composition which comprises a hair conditioning proportion of a quaternary ammonium salt hair conditioning agent, a surface active proportion of an anionic synthetic organic surface active agent, a normally solid water insoluble polyethylene in a proportion sufficient to increase the fiber conditioning effect of the quaternary ammonium salt when the polyethylene is solubilized, so as to be dispersible in water, and a solubilizing proportion of a normally liquid hydrocarbon or a mixture of hydrocarbons which is a solubilizer for the polyethylene and which helps to make it water dispersible in the presence of the quaternary ammonium salt, anionic synthetic organic detergent and water.

2. A hair conditioning composition according to claim 1, which is a shampoo and which comprises 8 to 25% of a water soluble lipophile sulfate and/or sulfonate of 8 to 20 carbon atoms in the lipophilic group, 0.1 to 3% of a quaternary ammonium halide of the formula $R^1 R^2 R^3 R^4 N^+ X^-$, wherein $R^1$ is lower alkyl of 1 to 4 carbon atoms, $R^2$ and $R^3$ are higher alkyls of 10 to 40 carbon atoms, $R^4$ is such a lower alkyl or such a higher alkyl, and X is a halogen, 0.2 to 5% of a polyethylene which is normally a solid at room temperature, 0.1 to 10% of a mineral oil which is a liquid at room temperature, 0.1 to 30% of adjuvant(s) and 50 to 95% of water.

3. A shampoo according to claim 2 which comprises 8 to 20% of a water soluble lipophile sulfate and/or sulfonate of 8 to 18 carbon atoms in the lipophilic group, in which the salt forming cation is ammonium, lower alkanolammonium or alkali metal, 0.2 to 2% of a quaternary ammonium halide wherein the sum of the carbon atoms is at least 30 and X is chlorine or bromine, 0.2 to 2% of a normally solid polyethylene of molecular weight in the range of 1,000 to 5,000, 0.2 to 8% of mineral oil of a molecular weight in the range of 150 to 1,000, 0.5 to 20% of adjuvant(s), and 60 to 90% of water.

4. A shampoo according to claim 3 which comprises 8 to 20% of a water soluble lipophile sulfate or mixture thereof of 10 to 18 carbon atoms in the lipophilic group, 0.3 to 1% of a quaternary ammonium halide wherein $R^1$ is alkyl of 1 or 2 carbon atoms, $R^2$, $R^3$ and $R^4$ are each alkyls of 12 to 22 carbon atoms, and the sum of the carbon atoms is at least 34, 0.2 to 1.5% of a normally solid polyethylene of molecular weight in the range of 1,000 to 4,000, 0.5 to 6% of mineral oil of a molecular weight in the range of 300 800, 3 to 15% of adjuvant(s) and 65 to 80% of water, which is of a viscosity in the range of 1,000 to 15,000 centipoises at 25° C. and a pH in the range of 5 to 8.

5. A shampoo according to claim 4 which comprises 10 to 15% of an alcohol sulfate of 10 to 18 carbon atoms, 1 to 5% of an alcohol ether sulfate of 10 to 18 carbon atoms, 0.3 to 0.7% of a quaternary ammonium chloride wherein $R^1$ is methyl and $R^2$, $R^3$ and $R^4$ are each alkyls of 12 to 18 carbon atoms, 0.5 to 1% of a normally solid polyethylene of molecular weight in the range of 1,000 to 3,500, 0.7 to 5% of mineral oil of a molecular weight in the range of 400 to 700, 3 to 15% of adjuvant(s) and 65 to 80% of water, which is of a viscosity in the range of 3,000 to 8,000 centipoises at 25° C. and a pH in the range of 6 to 7.

6. A hair conditioning composition according to claim 1 which is a shampoo which comprises 8 to 25% of a water soluble lipophile sulfate and/or sulfonate of 8 to 20 carbon atoms in the lipophilic group, 0.1 to 3% of a quaternary ammonium halide of the formula $R^1 R^2 R^3 R^4 N^+ X^-$, wherein $R^1$ is lower alkyl of 1 to 4 carbon atoms, $R^2$ and $R^3$ are higher alkyls of 10 to 40 carbon atoms, $R^4$ is such a lower alkyl or such a higher alkyl, and X is a halogen, 0.2 to 5% of a polyethylene which is normally a solid at room temperature, 0.1 to 10% of mineral oil which is a liquid at room temperature, 0.1 to 2% of paraffin of 20 to 60 carbon atoms, 0.1 to 2% of isoparaffin of 10 to 18 carbon atoms, 0.05 to 1.5% of cellulosic thickening agent, 0.5 to 6% of higher fatty acid lower alkanolamide, 0.5 to 1.5% of lower alkylene glycol higher fatty acid ester, 0.1 to 1% of higher fatty acid ester higher fatty alcohol, 0.3 to 2% of $C_{18-36}$ acid triglyceride, 0.2 to 1% of a preservative, up to 1.0% of alkali metal chloride and 50 to 90% of water.

7. A shampoo according to claim 6 which comprises 8 to 35% of a water soluble lipophile sulfate or mixture thereof of 10 to 18 carbon atoms in the lipophilic group, 0.3 to 1% of a quaternary ammonium halide wherein $R^1$ is alkyl of 1 or 2 carbon atoms, $R^2$, $R^3$ and $R^4$ are each alkyls of 12 to 22 carbon atoms and the sum of the carbon atoms in $R^1$, $R^2$, $R^3$ and $R^4$ is at least 34, 0.2 to 2% of a normally solid polyethylene of molecular weight in the range of 1,000 to 4,000, 0.5 to 6% of a mineral oil of a molecular weight in the range of 300 to 800, 0.1 to 1% of paraffin of 20 to 50 carbon atoms, 0.1 to 1% of isoparaffin of 12 to 16 carbon atoms, 0.2 to 1% of cellulosic thickening agent, 2 to 5% of higher fatty acid lower alkanolamide, 0.5 to 1% of ethylene glycol higher fatty acid ester, 0.1 to 0.6% of higher fatty acid ester of higher fatty alcohol, 0.5 to 1.5% of $C_{18-36}$ acid triglyceride, 0.3 to 0.7% of a preservative, up to 0.5% of alkali metal chloride and 65 to 80% of water, which shampoo is of a viscosity in the range of 1,000 to 10,000 centipoises at 25° C.

8. A shampoo according to claim 7 which comprises 10 to 15% of alcohol sulfate of 10 to 18 carbon atoms, 0 to 5% of higher alcohol ether sulfate of 10 to 18 carbon atoms, 0.3 to 0.7% of a quaternary ammonium chloride wherein $R^1$ is methyl and $R^2$, $R^3$ and $R^4$ are each alkyls of 12 to 18 carbon atoms, 0.2 to 1.0% of a normally solid polyethylene of molecular weight in the range of 2,000 to 3,500 0.7 to 5% of mineral oil of molecular weight in the range of 400 to 700, 0.1 to 0.5% of paraffin of 20 to 40 carbon atoms, 0.1 to 0.5% of isoparaffin of 13 to 14 carbon atoms, 0.4 to 0.8% of a hydroxy-lower alkyl cellulose thickening agent, 2 to 4% of higher fatty acid monoethanolamide, 0.5 to 1% of ethylene glycol higher fatty acid diester, 0.2 to 0.5% of higher fatty acid ester of higher fatty alcohol, 0.5 to 1% of $C_{18-36}$ acid triglyceride 0.4 to 0.6% of a preservative, up to 0.5% of sodium chloride and 65 to 80% of water, which shampoo is of a viscosity in the range of 3,000 to 8,000 centipoises at 25° C.

9. A shampoo according to claim 8 which comprises about 12.5% of ammonium lauryl sulfate, about 2.5% of sodium lauryl diethoxy ether sulfate, about 0.5% of tricetyl methyl ammonium chloride, about 0.8% of a normally solid polyethylene of molecular weight averaging about 2,100 about 1% of a mineral oil of molecular weight averaging about 550, about 0.4% of paraffin of 20 to 40 carbon atoms, about 0.3% of isoparaffin of 13 to 14 carbon atoms, about 0.6% of a hydroxymethyl cellulose or mixture of hydroxymethyl celluloses, about 3.5% of lauric monoethanolamide, about 0.8% of ethylene glycol distearate, about 0.4% of stearyl stearate, about 0.8% of $C_{18-36}$ acid triglyceride, about 0.5% of preservative, up to about 0.5% of sodium chloride and about 73% of water, which shampoo is of a viscosity of about 3,500 centipoises at 25° C.

10. A process for shampooing and conditioning hair which comprises shampooing the hair on one's head with a shampooing quantity of a composition according to claim 1, rinsing the hair after such shampooing and drying it, thereby leaving it conditioned due to the conditioning effects of the quaternary ammonium halide, polyethylene and mineral oil, in combination.

11. A process according to claim 10 wherein the shampoo comprises 8 to 20% of a water soluble sulfate or mixture thereof of 10 to 18 carbon atoms in the lipophilic group(s), 0.3 to 1% of a quaternary ammonium halide wherein $R^1$ is alkyl of 1 or 2 carbon atoms, $R^2$, $R^3$ and $R^4$ are each alkyls of 12 to 22 carbon atoms, and the sum of the carbon atoms is at least 34, 0.2 to 1.5% of a normally solid polyethylene of molecular weight in the range of 1,000 to 4,000, 0.5 to 6% of mineral oil of a molecular weight in the range of 300 to 800, 3 to 15% of adjuvant(s) and 65 to 80% of water, which is of a viscosity in the range of 1,000 to 15,000 centipoises at 25° C. and a pH in the range of 5 to 8, the shampoo is maintained in contact with the hair for one to five minutes, is rinsed with water and wet combed and is dried and dry combed or brushed.

12. A process according to claim 11 wherein the shampoo comprises 10 to 15% of alcohol sulfate of 10 to 18 carbon atoms, 1 to 5% of alcohol ether sulfate of 10 to 18 carbon atoms, 0.3 to 0.7% of a quaternary ammonium chloride wherein $R^1$ is methyl and $R^2$, $R^3$ and $R^4$ are each alkyls of 12 to 22 carbon atoms, 0.2 to 1.0% of a normally solid polyethylene of molecular weight in the range of 2,000 to 3,500, 0.7 to 5% of mineral oil of molecular weight in the range of 400 to 700, 0.1 to 1% of paraffin of 20 to 60 carbon atoms, 0.1 to 1% of isoparaffin of 10 to 18 carbon atoms, 0.4 to 0.8% of a hydroxy-lower alkyl cellulose thickening agent, 2 to 4% of higher fatty acid monoethanolamide, 0.5 to 1% of ethylene glycol of higher fatty acid diester, 0.2 to 0.5% of higher fatty acid ester of higher fatty alcohol, 0.5 to 1% of $C_{18-36}$ acid triglyceride, 0.4 to 0.6% of preservative, 0.2 to 0.4% of sodium chloride and 65 to 80% of water, which shampoo is of a viscosity in the range of 3,000 to 8,000 centipoises at 25° C. and is of a pH in the range of 6 to 7, and is applied to the hair and scalp of a user in amount in the range of 2 to 15 grams per use.

13. A process for the manufacture of a hair conditioning shampoo of claim 2 which comprises forming a dispersion or emulsion of water soluble lipophile sulfate and/or sulfonate and adjuvants in water at an elevated temperature, dissolving and/or dispersing quaternary ammonium halide and normally solid polyethylene in mineral oil at elevated temperature and admixing the two described pre-mixes to form a stable dispersion or emulsion.

14. A process according to claim 13 wherein the shampoo comprises 10 to 15% of alcohol sulfate of 10 to 18 carbon atoms, 1 to 5% of alcohol ether sulfate of 10 to 18 carbon atoms, 0.3 to 0.7% of a quaternary ammonium chloride of the formula $R^1 R^2R^3R^4 N^+ Cl^-$ wherein $R^1$ is methyl and $R^2$, $R^3$ and $R^4$ are each alkyls of 12 to 18 carbon atoms, 0.2 to 1.0% of a normally solid polyethylene of molecular weight in the range of 1,000 to 3,500, 0.7 to 5% of mineral oil of molecular weight in the range of 400 to 700, 0.1 to 0.5% of paraffin of 20 to 40 carbon atoms, 0.1 to 0.5% of isoparaffin of 13 to 14 carbon atoms, 0.4 to 0.8% of a hydroxy-lower alkyl cellulose thickening agent, 2 to 4% of higher fatty acid monoethanolamide, 0.5 to 1% of ethylene glycol higher fatty acid diester, 0.2 to 5% of higher fatty acid ester of higher fatty alcohol, 0.5 to 1% of $C_{18-36}$ acid triglyceride, 0.4 to 0.6% of preservative, up to 0.5% of sodium chloride and 65 to 80% of water, which shampoo is of a viscosity in the range of 3,000 to 8,000 centipoises at 25° C., the two pre-mixes are at a temperature in the range of 70° to 90° C. when admixed, and they are stirred together at such a temperature for from 5 minutes to 1 hour, after which the resulting dispersion or emulsion is cooled to room temperature, and is in stable, non-separating and non-settling form, of a pH in the range of 6 to 7 and a viscosity in the range of 1,000 to 10,000 centipoises at 25° C., and is of greater conditioning power after shampooing than are control compositions of identical compositions that are made without admixing of the quaternary ammonium chloride, polyethylene and mineral oil at elevated temperature in the manner described herein.

* * * * *